US010746714B2

(12) United States Patent
Ba et al.

(10) Patent No.: US 10,746,714 B2
(45) Date of Patent: Aug. 18, 2020

(54) AIR POLLUTION SOURCE RECOGNITION BASED ON DYNAMIC PAIRING AND COMPARISON (71) Applicant: INTERNATIONAL BUSINESS MACHINES CORPORATION, Armonk, NY (US)

(72) Inventors: Yu Tao Ba, Beijing (CN); Ming Xie, Beijing (CN); Lingyun Wang, Beijing (CN); Ke Xu Zou, Beijing (CN); Wenchen Cheng, Beijing (CN); Gang Zhou, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 360 days.

(21) Appl. No.: 15/624,901

(22) Filed: Jun. 16, 2017

(65) Prior Publication Data
US 2018/0364208 A1    Dec. 20, 2018

(51) Int. Cl.
*G01N 33/00* (2006.01)
(52) U.S. Cl.
CPC ..... *G01N 33/0036* (2013.01); *G01N 33/0031* (2013.01); *G01N 33/0075* (2013.01)
(58) Field of Classification Search
CPC ........... G01N 33/0036; G01N 33/0037; G01N 33/0031; G01N 33/0004; G01N 33/0063; G01N 33/0075
See application file for complete search history.

(56) References Cited

U.S. PATENT DOCUMENTS

| 2013/0035860 A1* | 2/2013 | Guha | G01W 1/10 702/3 |
| 2013/0110400 A1* | 5/2013 | Moshe | G01N 1/26 702/3 |

(Continued)

FOREIGN PATENT DOCUMENTS

| CA | 2447756 A1 | 11/2002 |
| CN | 101847180 A | 9/2010 |

(Continued)

OTHER PUBLICATIONS

Henry, et al., "Locating Nearby Sources of Air Pollution by Nonparametric Regression of Atmospheric Concentrations on Wind Direction", NRCSE Technical Report Series, NRCSE-TRS No. 071, Sep. 21, 2001, pp. 1-21, Submitted to Atmospheric Environment Jul. 2001 published in vol. 36, Issue 13, May 2002, pp. 2237-2244.

(Continued)

*Primary Examiner* — Gregory J Toatley, Jr.
*Assistant Examiner* — Lynda Dinh
(74) *Attorney, Agent, or Firm* — Dmitri Paskalov (57) ABSTRACT A processor-implemented method receives a plurality of pollution measurement data, a plurality of geodetic data, and a plurality of meteorological data associated with a geographical area. The processor-implemented method generates a grid of the geographical area, whereby the generated grid virtually divides the geographical area into a plurality of cells. The processor-implemented method associates the received plurality of measurement data, the received plurality of geodetic data, and the received plurality of meteorological data with a cell in the generated grid. The processor-implemented method determines a pollutant contribution value of the cell based on the pollution measurement data associated with the cell and a physical contribution of a plurality of pollutants. The processor-implemented method identifies the pollution source based on a paired comparison (Continued)

of the plurality of cells and displays the location on the geographical area associated with the identified pollution source.

20 Claims, 6 Drawing Sheets

(56) References Cited

U.S. PATENT DOCUMENTS

2016/0125307 A1   5/2016  Zheng et al.
2016/0370333 A1   12/2016 Li et al.

FOREIGN PATENT DOCUMENTS

| CN | 102628852 A | 8/2012 |
| CN | 104200104 A | 12/2014 |
| CN | 104597212 A | 5/2015 |
| CN | 104950037 A | 9/2015 |
| CN | 105608697 A | 5/2016 |

OTHER PUBLICATIONS

Chen, et al., "A New Air Pollution Sources Identification Method Based on Remotely Sensed Aerosol and Swarm Intelligence", Published in Geoscience and Remote Sensing Symposium (IGARSS), 2016 IEEE International, Jul. 10-15, 2016, pp. 4131-4314.

Mell et al., "The NIST Definition of Cloud Computing," U.S. Department of Commerce, National Institute of Standards and Technology, Sep. 2011, p. 1-7, Special Publication 800-145.

* cited by examiner

| Grid Cell No. | Longitude | Latiotude | Mountain [%] | Urban [%] | Crop [%] | Forest [%] | Grass[%] | Water[%] | Date and Time | Temperature | Humidity | Pressure |
|---|---|---|---|---|---|---|---|---|---|---|---|---|
| 1 | 115.3537 | 41.348 | 10% | 95% | 0% | 2% | 2% | 0% | 1/12/2017 1:00 | -3.00 | 30.00 | 1.10 |
| ... | ... | ... | ... | ... | ... | ... | ... | ... | ... | ... | ... | ... |

SPATIAL FEATURES 222    TEMPORAL FEATURES 224

FIG. 2B

| Grid Cell No. | Paired Cells | Date and Time | Contribution | Mean Value Of The Paired Cells |
|---|---|---|---|---|
| 1 | 1,5,8,13,23,42,... | 1/12/2017 1:00 | 513 | 413 |
| 1 | 1,5,8,13,23,42,... | 1/12/2017 2:00 | 488 | 401 |
| 1 | 1,5,8,13,23,42,... | 1/12/2017 3:00 | 612 | 488 |

AIR POLLUTION SOURCE RECOGNITION BASED ON DYNAMIC PAIRING AND COMPARISON

BACKGROUND

The present invention relates, generally, to the field of computing, and more particularly to determining an air pollution source.

Typically, air pollution consists of atmospheric particulate matter. The particulate matter (PM) is a microscopic solid or liquid matter suspended in the atmosphere of the earth. A mixture of an air and PM is an aerosol. The aerosol and PM have not only an impact on climate and precipitation but also adversely affect human health.

SUMMARY

According to one embodiment, a method, computer system, and computer program product for determining an air pollution source that is based on gridding a geographical area and pairing and comparison of the gridded cells is provided. A processor-implemented method may receive a plurality of pollution measurement data, a plurality of geodetic data, and a plurality of meteorological data associated with a geographical area. The processor-implemented method may generate a grid of the geographical area, whereby the generated grid virtually divides the geographical area into a plurality of cells. The processor-implemented method may associate the received plurality of measurement data, the received plurality of geodetic data, and the received plurality of meteorological data with a cell in the generated grid. The processor-implemented method may determine a pollutant contribution value of the cell based on the pollution measurement data associated with the cell and a physical contribution of a plurality of pollutants. The processor-implemented method may identify the pollution source based on a paired comparison of the plurality of cell s and displays the location on the geographical area associated with the identified pollution source.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate to the field of computing, and more particularly to determining an air pollution source. The following described exemplary embodiment provides a system, method, and program product to, among other things, determine an air pollution emission source based on gridding an area and dynamically comparing the gridded cells after subtracting physical transportation and secondary formation criteria that affect the measurements. Therefore, the present embodiment has the capacity to improve the technical field of determining an air pollution source by locating even scattered sources of pollution with momentary emissions, and is also capable of determining an air pollution source in heavily polluted geographic areas.

As previously described, air pollution consists of atmospheric particulate matter (PM). The PM is a microscopic solid or a liquid matter suspended in the atmosphere of the earth. A mixture of air and PM is an aerosol. The aerosol and PM have not only impact on climate and precipitation but also adversely affect human health.

Typically, air pollution is generated from emission sources. Emission sources may be grouped into four categories: point, mobile, biogenic and aerial. Point sources are generally sources that have a static geographic location at a specific area, such as factories, electrical power plants or other industrial facilities. Mobile sources are sources that have a mobile emission location, such as cars, planes, and trucks. Biogenic emission sources are emissions that come from natural sources, such as emissions from vegetation, volcanic emissions, or sea salt emissions. Aerial sources may be a specific, man-made areas that emit pollution, such as a road, a contaminated water reservoir, or a forest fire.

Additionally, air pollution is generated not only produced from emission sources but also from secondary formation and physical transportation effects. A secondary formation effect is, typically, a chemical process that occurs when the pollutant from the emission source interacts with Earth's atmosphere. For example, ozone, which is formed when hydrocarbons (HC) and nitrogen oxides (NOx) combine in the presence of a sunlight, such as $NO_2$ that is formed when NO combines with oxygen in the open air, or an acid rain, which is formed when sulfur dioxide or nitrogen oxides react with water reservoirs. After generation, air pollution is mixed and spread via the atmosphere, by physical transportation effects. Physical transportation effects may be a wind, humidity, pressure changes, or other physical processes that may move the pollutant in the atmosphere.

Typically, the pollution is measured using diffusion tubes, spectroscopic, gas or combined techniques that are stationed at specific locations within the geographical area. These measurements may provide a general pollution condition of the atmosphere but lack the ability to locate the scattered emission sources with momentary (short time) emissions, especially in a heavy polluted conditions. As such, it may be advantageous to, among other things, implement a system that determines a geographic location of an air pollution source by separating the area of interest into gridded cells in order to determine the location of the of the scattered emission sources.

According to one embodiment, a processor-implemented method receives pollution measurement data, geodetic data, and meteorological data associated with an area. A grid of the area may be generated and the measurement data, the geodetic data, and the meteorological data may be associated with one or more gridded cells, where the gridded cells may virtually divide the area into the one or more gridded cells. A pollutant contribution value of the one or more gridded cells may then be calculated. Next, the pollution source may be identified based on physical transportation effect elimination and a paired comparison of the gridded cells. The grid with the identified pollution source may then be displayed to a user to indicate the location associated with the identified pollution source.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to identify an exact location of an air pollution emission source. The method is based on gridding the geographical area into cells and after subtracting physical transportation effects from measurements of the air pollution in each cell, determining the emission source by comparing the gridded cells having similar features in order to eliminate secondary formation effect contributions to the measurements in each cell.

Figure 1:
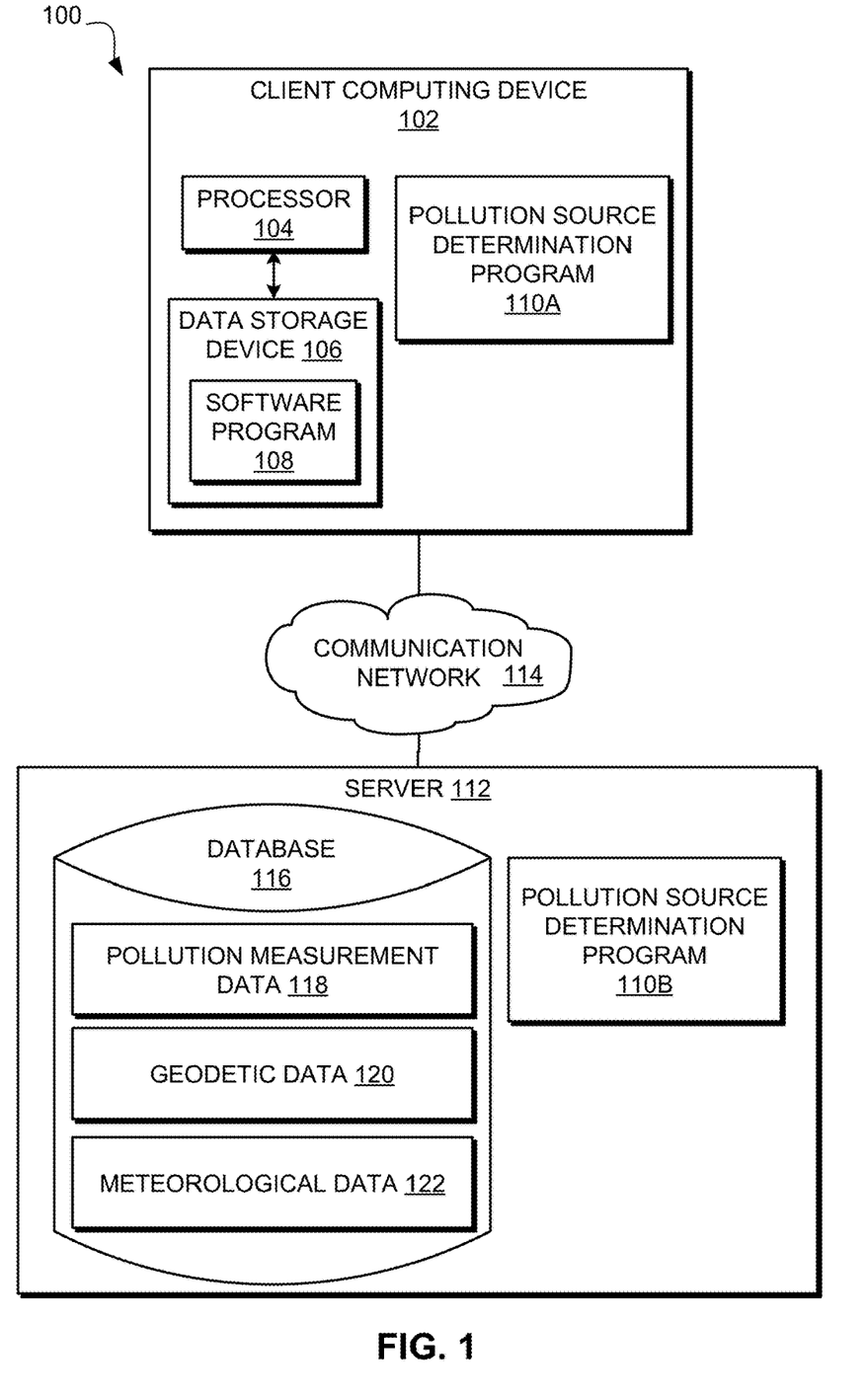
FIG. 1 illustrates an exemplary networked computer environment according to at least one embodiment.

Referring to FIG. 1, an exemplary networked computer environment 100 is depicted, according to at least one embodiment. The networked computer environment 100 may include client computing device 102 and a server 112 interconnected via a communication network 114. According to at least one implementation, the networked computer environment 100 may include a plurality of client computing devices 102 and servers 112, of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

Client computing device 102 may include a processor 104 and a data storage device 106 that is enabled to host and run a software program 108 and a pollution source determination (PSD) program 110A and communicate with the server 112 via the communication network 114, in accordance with one embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 3, the client computing device 102 may include internal components 302a and external components 304a, respectively.

The server computer 112 may be a laptop computer, netbook computer, personal computer (PC), a desktop computer, or any programmable electronic device or any network of programmable electronic devices capable of hosting and running a PSD program 110B and a database 116 and communicating with the client computing device 102 via the communication network 114, in accordance with embodiments of the invention. As will be discussed with reference to FIG. 3, the server computer 112 may include internal components 302b and external components 304b, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

Database 116 may be a data repository capable of storing information, such as pollution measurement data 118, geodetic data 120, and meteorological data 122. Pollution measurement data 118 may be pollution measurement data from a high-density sensor network. High density sensor networks are networks of sensors spread over a geographical area and configured to measure air pollution. For example, pollution measurement data 118 may be received from high density sensor networks that exists in major cities, airports and other facilities, such as NCore multipollutant monitoring network. In another embodiment, other data from various sensors may be used to determine pollution, such as speed of sound sensors, odor sensors or light sensors that may be connected to communication network 114 and capable of sending measurements to server 112 and stored in database 116 or entered manually by a user. The pollution measurement data 118 may include fields such as: date when the measurement was taken, time of the measurement, location of the sensor, and magnitude of the pollution.

Geodetic data 120 may be data that incorporates geographical images of the area where pollution measurement data 118 where acquired and, also, may include a surface landscape, such as whether the surface is water, forest, or urban. For example, geodetic data 120 may be received from a satellite remote sensing, such as World Geodetic System (WGS) in WGS84 standard. A WGS84 standard is a broadly used standard in geodesy, cartography, and global positioning system (GPS) navigation on the surface of the earth. For example, geodetic data 120 may include a landscape data from the National Aeronautics and Space Administration (NASA) moderate-resolution imaging spectroradiometer (NASA MODIS) that provides 1 km×1 km (0.621 mile× 0.621 mile) resolution of the surface of the earth or NASA Landsat that is configured to provide a more detailed resolution of 50 m×50 m (164 feet×164 feet). A geodetic data 120 may include location statistical fields, such as coordinate system (longitude and latitude) and other data related to each region of the geographical area, such as coordinates, boundaries, and surface properties of each region. The size of the region typically depends on the resolution of the spectroradiometer. Surface properties may include percentage representation or other data that may be converted to a percentage representation of the surface type of the region such as a percentage of mounts in the region, a percentage of urban development in the region, a percentage of crop fields, forest, grass, and/or water.

A metrological data 122 may be data that incorporates meteorological conditions of the area where pollution measurement data 118 were acquired and include measurements of winds, wind directions, temperature, and humidity levels. According to the present embodiment, meteorological data 122 may be acquired either from sensors located at the geographic area or from a weather services database available over communication network 114, such as the Internet. In another embodiments, pollution measurement data 118, geodetic data 120, and/or meteorological data 122 may be located on data storage device 106 or loaded using internal components 302 a,b or external components 304 a,b.

Figure 2A:
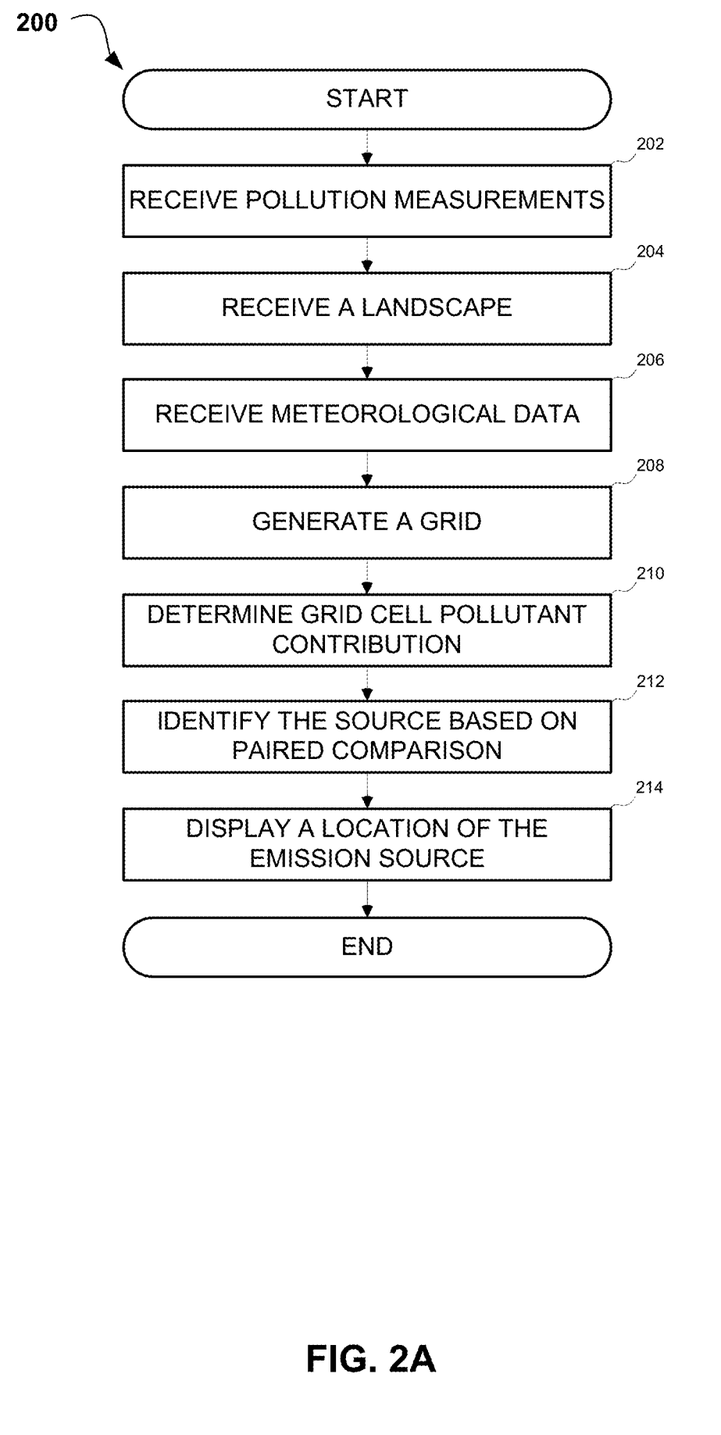
FIG. 2A is an operational flowchart illustrating an air pollution source determination process according to at least one embodiment.

According to the present embodiment, the PSD program 110A, 110B may be a program capable of determining a location of a pollution source based on gridding an area, determining pollutant contribution values in each gridded cell, and determining the pollution source location based on determining the actual pollution in each gridded cell by subtracting physical transportation and secondary formation effects based on dynamic pairing and comparison between gridded cells. The air pollution source recognition based on dynamic pairing and comparison method is explained in further detail below with respect to FIG. 2.

Referring now to FIG. 2, an operational flowchart illustrating an air pollution source determination process 200 is depicted according to at least one embodiment. At 202, the PSD program 110A, 110B receives pollution measurements. According to the present embodiment, PSD program 110A, 110B may access pollution measurement data 118 from database 116. In another embodiment, PSD program 110A, 110B may receive pollution measurement data 118 from communication network 114, such as the Internet. For example, pollution measurement data 118 may be received from air quality monitoring agencies, such as United States Environmental Protection Agency (EPA).

Next, at 204, PSD program 110A, 110B receives a landscape of the area. According to the present embodiment, PSD program 110A, 110B may receive a landscape information from geodetic data 120 stored in database 116. In another embodiment, PSD program 110A, 110B may receive geodetic data 120 from communication network 114, such as the Internet. For example, geodetic data 120 may be received from United States Geological survey (USGS) Landsat database.

Next, at 206, PSD program 110A, 110B receives meteorological data. According to the present embodiment, PSD program 110A, 110B may receive meteorological data meteorological data 122 stored in database 116. In another embodiment, PSD program 110A, 110B may receive meteorological data 122 from communication network 114, such as the Internet. For example, meteorological data 122 may be received from National Oceanic and Atmospheric Administration national weather service database.

Next at 208, PSD program 110A, 110B generates a grid of the area. According to the present embodiment, PSD program 110A, 110B may combine the pollution measurement data 118, geodetic data 120 and meteorological data 122 and grid the area into gridded cells. The gridded cells may be square shaped while the size of each cell may be limited by the resolution of geodetic data 120. For example, if the geodetic data 120 was received from the NASA Landsat database, the smallest gridded cell dimensions are limited to 50 m×50 m (164 feet×164 feet). According to the present embodiment, PSD program 110A, 110B may organize the grid in a table that contains the following fields as described in FIG. 2B: gridded cell number, latitude, longitude, mountain, urban, crop, forest, grass, water, time, temp, humidity, and pressure. A gridded cell number is a unique gridded cell identification number. Longitude and latitude are the coordinates of the gridded cell. Mountain, urban, crop, forest, and water are spatial features that represent the percentage of land type in the gridded cell. In another embodiment, the gridded cell type values may be estimated based on geodetic data 120 analysis, such as image processing of each gridded cell. For example, PSD program 110A, 110B may analyze the digital image of the gridded cell and determine a percentage of forest in the grid based on a ratio of the green area to the gridded cell area. Time represents a date and time when the measurement of the pollution was taken. Temperature, humidity, and pressure are temporal features that represent the air temperature, humidity, and pressure of the air inside the gridded cell. In another embodiment, the grid may be of different sizes and shapes and the cells may partially overlap each other.

Next at 210, PSD program 110A, 110B determines a gridded cell pollutant contribution. According to the present embodiment, PSD program 110A, 110B may calculate the pollution contribution that consists of an original emission of the gridded cell and a secondary formation of pollutant inside the gridded cell by excluding the physical transportation of pollutant from adjoining gridded cells. The gridded cell pollutant contribution may be calculated using the equations:

$$PT(t, i) = HT(t, i) + VT(t, i)$$

$$HT(t, i) = \frac{-SpatGrad(t, i) * DirHW * SpeedHW}{Grid}$$

$$VT(t, i) = \frac{Pollution(t, i) * SpeedVW}{Grid}$$

$$\Delta Pollution(t, i) = Pollution(t, i) - Pollution(t-1, i)$$

$$\text{Pollutant Contribution} = \Delta Pollution(t, i) - PT(t, i)$$

where PT is Physical Transportation of the pollutant, t is the time of the measurements, i is a gridded cell number, HT is a Horizontal Transportation, VT is a vertical transportation, SpatGrad is a spatial gradient of the pollution, DirHW is a direction of horizontal wind, and SpeedHW is a speed of horizontal wind.

Next at 212, PSD program 110A, 110B identifies the source based on a paired comparison between gridded cells. According to the present embodiment, PSD program 110A, 110B may determine the location, date, and time of the emission source based on static and dynamic feature comparisons between paired gridded cells using a similarity coefficient in order to eliminate pollution contributions due to secondary formation in the gridded cells. Similarity coefficient of gridded cells may be determined based on an equation:

$$\text{Similarity}(i,j) = 1/\Sigma w |\text{features}(i) - \text{features}(j)|,$$

where i and j are gridded cell numbers identifying each gridded cell, features are grouped into spatial or temporal features of the gridded cells, w is a user-defined weight associated with each feature, and $\|$ is a distance function. Static comparison is based on determining paired gridded cells with high static similarity of the spatial features of paired gridded cells. For example, if the Similarity function of gridded cells i and j is above a static threshold value determined by the user, then the gridded cells have static similarity. After determining the paired gridded cells having static similarity, PSD program 110A, 110B may compare between the gridded cells, pollutant contribution values, and a mean pollutant contribution value of gridded cells having a high dynamic similarity, where the dynamic similarity is determined by calculating the Similarity function of gridded cells i and j based on temporal features of the gridded cells. The gridded cells having a higher pollution contribution value with statistical significance ($p<0.05$) are the gridded cells having the emission sources. The statistical significance may be determined by comparing the gridded cell pollutant contribution value over time to a mean pollutant contribution values of paired gridded cells as shown in FIG. 2C.

Next at 214, PSD program 110A, 110B displays a location of the emission source. According to the present embodiment, PSD program 110A, 110B may display the location of the emission source based on the longitude and altitude associated with the cell where the emission contribution is the highest. For example, PSD program 110A, 110B may display the gridded landscape where the contribution values of the cells are represented as colors (a heat map). In another embodiment, PSD program 110A, 110B may determine the longitude and latitude of the cells having contribution values above a threshold value. In further embodiments, PSD program 110A, 110B may display a table of all the cells where contribution values are above threshold and convert the longitude and the latitude to a GPS format.

Figure 2B:
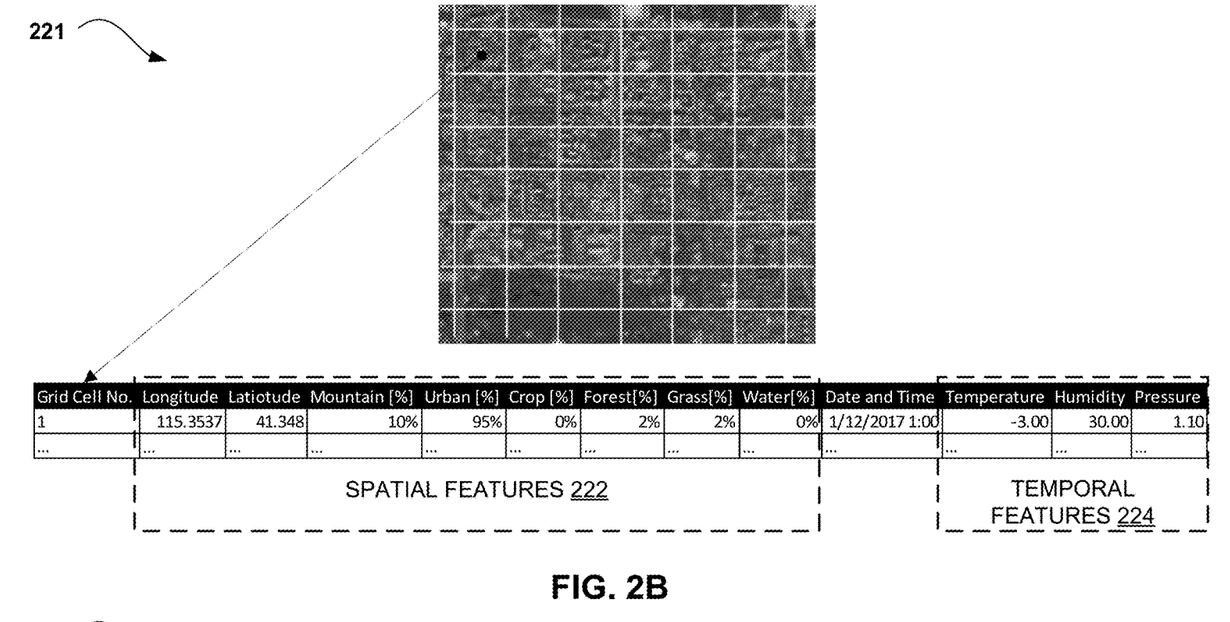
FIG. 2B illustrates an exemplary grid of a geographic area and a gridded cell with features according to at least one embodiment.
Figure 2C:
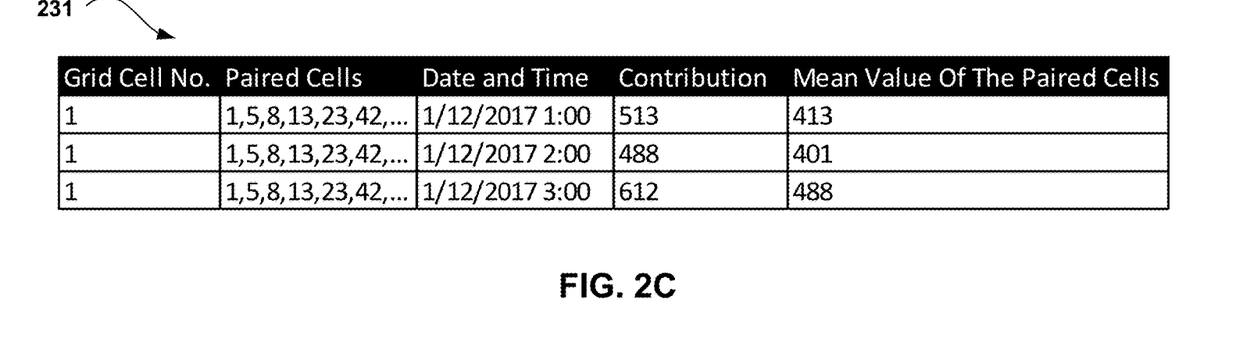
FIG. 2C illustrates an exemplary pollution contribution values comparison table of the gridded cells according to at least one embodiment.

FIG. 2B illustrates an exemplary grid 221 of a geographic area and typical features of each according to at least one embodiment. The features of each cell may be divided to spatial features 222 and temporal features 224. Spatial features 222 represent a percentage of land type features of the landscape of the cell, such as mountain, urban, crop, forest, grass, and water. Temporal features 224 represent features of the air, such as temperature, humidity, and pressure of the air in the cell.

FIG. 2C illustrates an exemplary pollution contribution values comparison table 231 of the gridded cells according to at least one embodiment. The pollution contribution values comparison table 231 may include fields of a current grid cell number, paired cells that were identified by PSD program 110A, 110B that are similar to the grid cell number, date and time the measurements were taken, a contribution of the current cell to the pollution, and the mean value of the paired cells.

It may be appreciated that FIGS. 2A-2C provide only an illustration of one implementation and does not imply any limitations with regard to how different embodiments may be implemented. Many modifications to the depicted environments may be made based on design and implementation requirements.

Figure 3:
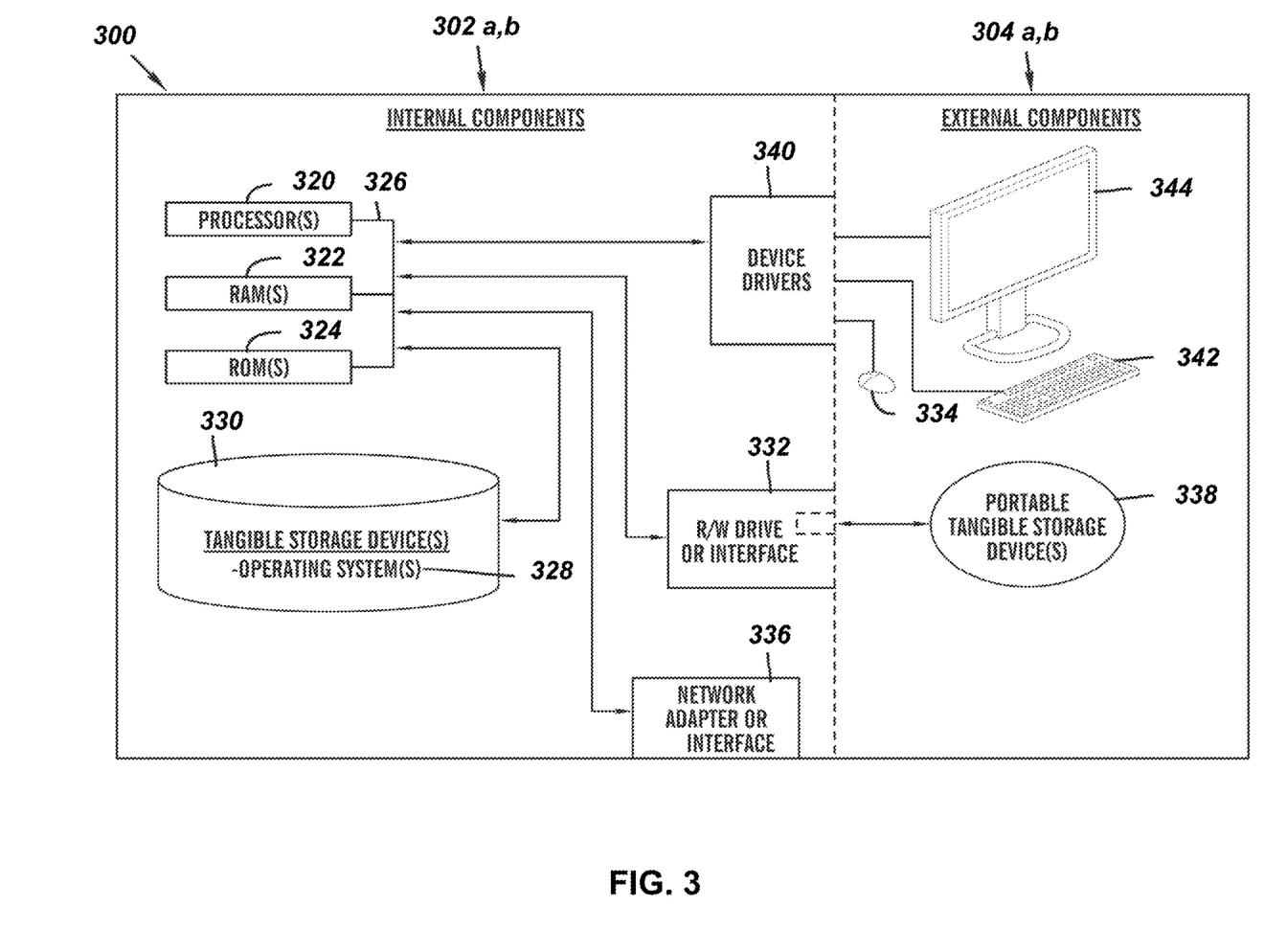
FIG. 3 is a block diagram of internal and external components of computers and servers depicted in FIG. 1 according to at least one embodiment.

FIG. 3 is a block diagram 300 of internal and external components of the client computing device 102 and the server 112 depicted in FIG. 1 in accordance with an embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

The data processing system 302, 304 is representative of any electronic device capable of executing machine-readable program instructions. The data processing system 302, 304 may be representative of a smart phone, a computer system, PDA, or other electronic devices. Examples of computing systems, environments, and/or configurations that may represented by the data processing system 302, 304 include, but are not limited to, personal computer systems, server computer systems, thin clients, thick clients, handheld or laptop devices, multiprocessor systems, microprocessor-based systems, network PCs, minicomputer systems, and distributed cloud computing environments that include any of the above systems or devices.

The client computing device 102 and the server 112 may include respective sets of internal components 302 a,b and external components 304 a,b illustrated in FIG. 3. Each of the sets of internal components 302 include one or more processors 320, one or more computer-readable RAMs 322, and one or more computer-readable ROMs 324 on one or more buses 326, and one or more operating systems 328 and one or more computer-readable tangible storage devices 330. The one or more operating systems 328, the software program 108 and the PSD program 110A in the client computing device 102, and the PSD program 110B in the server 112 are stored on one or more of the respective computer-readable tangible storage devices 330 for execution by one or more of the respective processors 320 via one or more of the respective RAMs 322 (which typically include cache memory). In the embodiment illustrated in FIG. 3, each of the computer-readable tangible storage devices 330 is a magnetic disk storage device of an internal hard drive. Alternatively, each of the computer-readable tangible storage devices 330 is a semiconductor storage device such as ROM 324, EPROM, flash memory or any other computer-readable tangible storage device that can store a computer program and digital information.

Each set of internal components 302 a,b also includes a R/W drive or interface 332 to read from and write to one or more portable computer-readable tangible storage devices 338 such as a CD-ROM, DVD, memory stick, magnetic tape, magnetic disk, optical disk or semiconductor storage device. A software program, such as the cognitive screen protection program 110A, 110B, can be stored on one or more of the respective portable computer-readable tangible storage devices 338, read via the respective R/W drive or interface 332, and loaded into the respective hard drive 330.

Each set of internal components 302 a,b also includes network adapters or interfaces 336 such as a TCP/IP adapter cards, wireless Wi-Fi interface cards, or 3G or 4G wireless interface cards or other wired or wireless communication links. The software program 108 and the PSD program 110A in the client computing device 102 and the PSD program 110B in the server 112 can be downloaded to the client computing device 102 and the server 112 from an external computer via a network (for example, the Internet, a local area network or other, wide area network) and respective network adapters or interfaces 336. From the network adapters or interfaces 336, the software program 108 and the PSD program 110A in the client computing device 102 and the PSD program 110B in the server 112 are loaded into the respective hard drive 330. The network may comprise copper wires, optical fibers, wireless transmission, routers, firewalls, switches, gateway computers and/or edge servers.

Each of the sets of external components 304 a,b can include a computer display monitor 344, a keyboard 342, and a computer mouse 334. External components 304 a,b can also include touch screens, virtual keyboards, touch pads, pointing devices, and other human interface devices. Each of the sets of internal components 302 a,b also includes device drivers 340 to interface to computer display monitor 344, keyboard 342, and computer mouse 334. The device drivers 340, R/W drive or interface 332, and network adapter or interface 336 comprise hardware and software (stored in storage device 330 and/or ROM 324).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
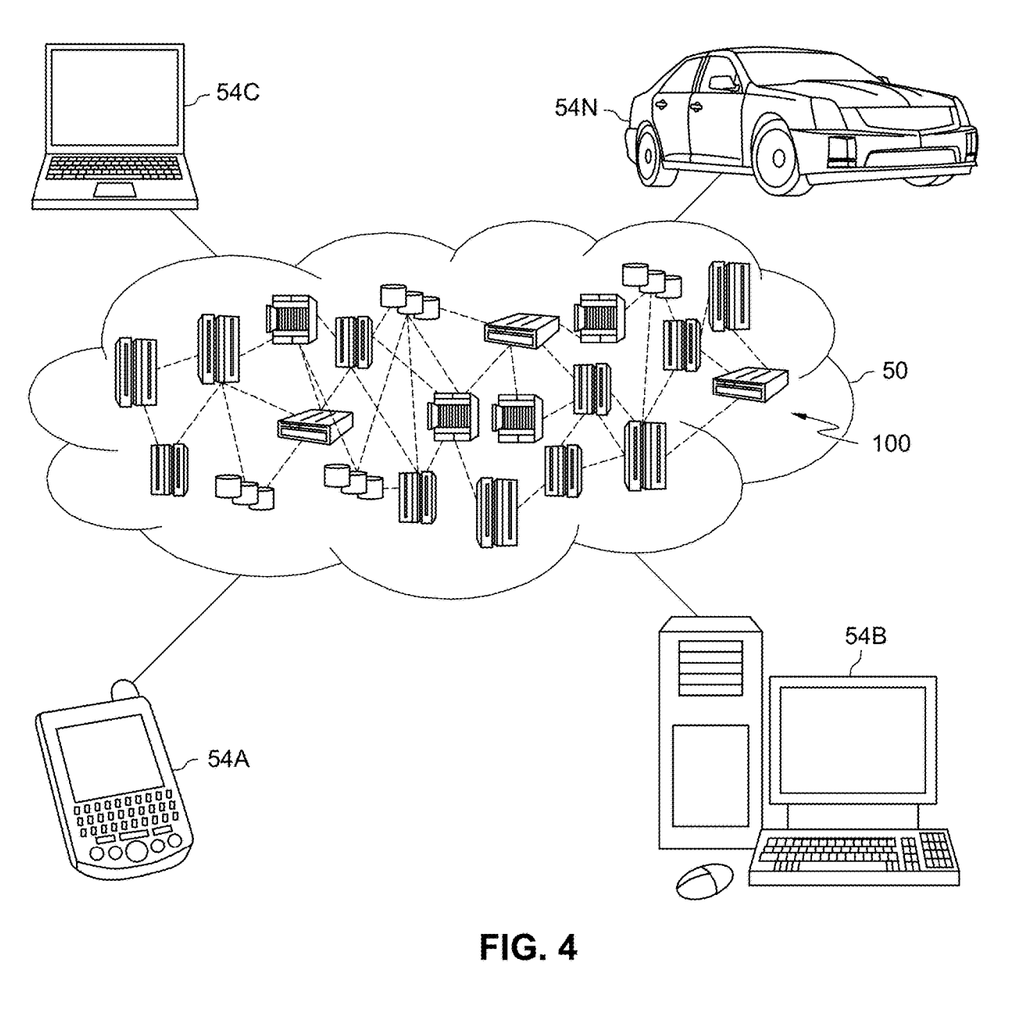
FIG. 4 depicts a cloud computing environment according to an embodiment of the present invention.

Referring now to FIG. 4, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 100 and cloud computing environment 50 can communicate with any type of computerized device over any type of network and/or network addressable connection (e.g., using a web browser).

Figure 5:
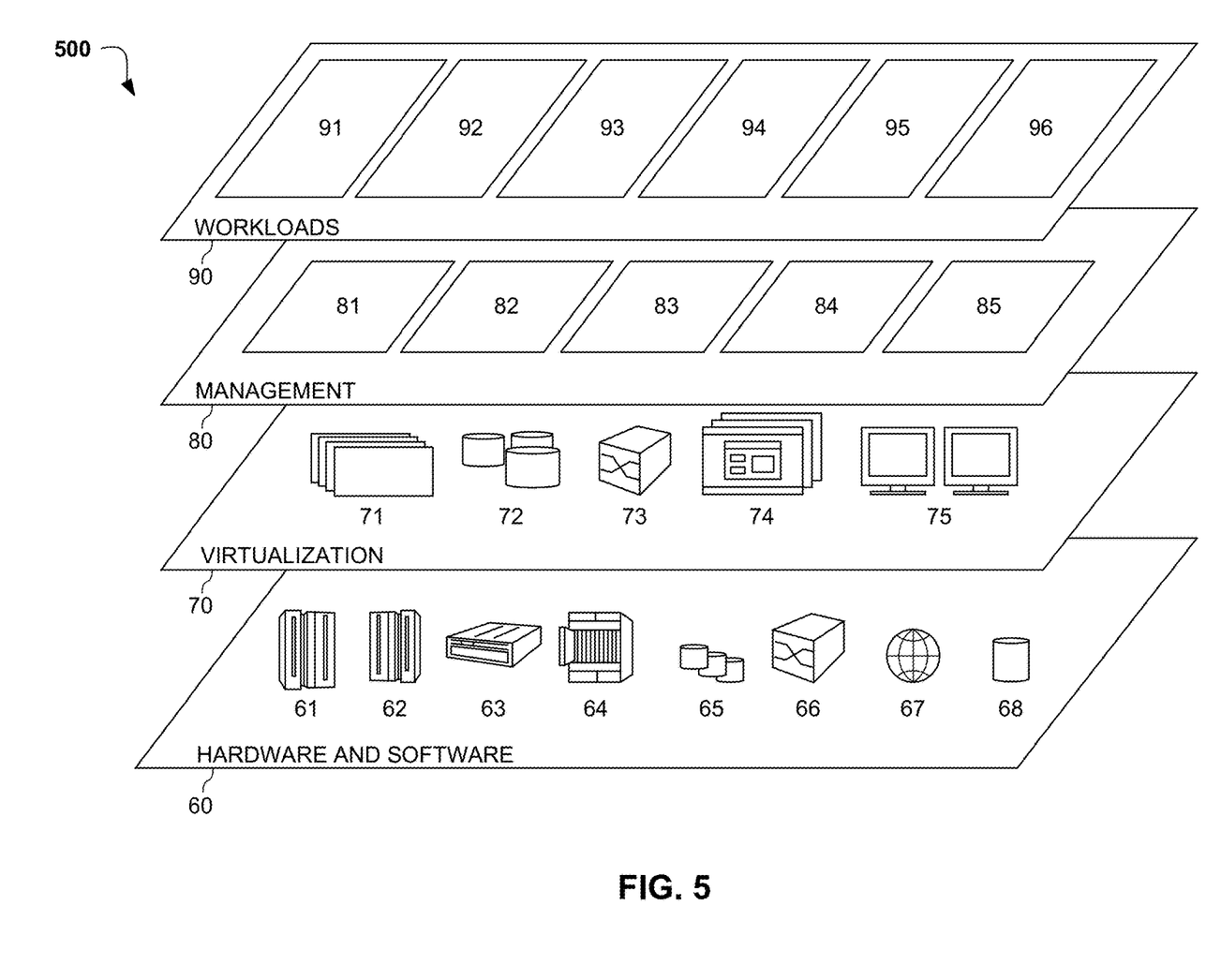
FIG. 5 depicts abstraction model layers according to an embodiment of the present invention.

Referring now to FIG. 5, a set of functional abstraction layers 500 provided by cloud computing environment 50 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and pollution source determination 96. Pollution source determination 96 may relate to determining a location of a pollution source based on gridding an area, determining pollutant contribution values in each gridded cell, and determining the pollution source location based on determining the actual pollution in each gridded cell by subtracting physical transportation and secondary formation effects based on dynamic pairing and comparison between gridded cells.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A processor-implemented method for determining a location of a pollution source, where pollution measurement data acquired from communication network includes one or more client computing devices and one or more servers, the method comprises:
   receiving, by the one or more client computing devices, the plurality of pollution measurement data of a geographical area, a plurality of geodetic data of the geographical area, and a plurality of meteorological data of the geographical area;
   generating, by the one or more client computing devices, a grid of the geographical area, wherein the generated grid virtually divides the geographical area into a plurality of cells;
   associating, by the one or more client computing devices, the plurality of the pollution measurement data, the plurality of the geodetic data, and the plurality of the meteorological data with one or more of the plurality of the cells in the generated grid;
   determining, by the one or more client computing devices, a pollutant contribution value of the one or more of the plurality of the cells based on subtracting a physical contribution of the plurality of pollutants from the pollution measurement data associated with the cell, wherein the pollutant contribution is calculated including an original emission of a pollutant and a secondary formation of the pollutant inside the one or more of the plurality of the cells excluding a movement of pollutant from adjoining cells;
   identifying, by the one or more client computing devices, the pollution source based on a paired comparison of the plurality of cells, wherein the paired comparison of the plurality of the cells to eliminate the pollution contributions due to the secondary formation in the cells; and
   displaying, by the one or more client computing devices, the location on the geographical area associated with the identified pollution source.

2. The method of claim 1, wherein determining the pollutant contribution value of the cell comprises:
   determining the physical contribution of a plurality of pollutants of the plurality of cells based on a vertical movement and a horizontal movement of the plurality of pollutants, wherein the vertical movement is determined by a vertical wind measurement extracted from the plurality of meteorological data, and wherein the horizontal movement is determined by a horizontal wind measurement extracted from the plurality of meteorological data; and
   calculating the pollutant contribution value of the cell based on subtracting the physical contribution of the plurality of pollutants from the pollution measurement data associated with the cell.

3. The method of claim 1, wherein identifying the pollution source based on the paired comparison of the plurality of cells comprises:
   determining a first cell from the plurality of cells based on a cell number;
   determining a second cell from the plurality of cells based on a similarity coefficient being above a static threshold value, wherein the similarity coefficient is determined based on spatial features of the first cell and the spatial features of the second cell;
   determining that a first cell pollution contribution value is higher than a second cell pollution contribution value; and
   based on determining the first cell pollution contribution value is higher than the second cell pollution contribution value, identifying the pollution source as the first cell.

4. The method of claim 3, wherein the spatial features are selected from a group consisting of a percentage representation of a plurality of mountains area within the plurality of cells, a percentage representation of a plurality of urban infrastructures area within the plurality of cells, a percentage representation of a plurality of crop fields area within the plurality of cells, a percentage representation of a forest area within the plurality of cells, a percentage representation of a plurality of grass fields area within the plurality of cells, and a percentage representation of a plurality of water reservoirs area within the plurality of cells.

5. The method of claim 3, wherein determining that the first cell pollution contribution value is higher than the second cell pollution contribution value comprises:

determining a dynamic similarity coefficient between the first cell and the second cell; and determining that the first cell pollution contribution value is higher than the second cell based on the dynamic similarity coefficient and the first cell pollution contribution value.

6. The method of claim 5, wherein the dynamic similarity coefficient is determined based on a plurality of temporal features of the first cell and a plurality of temporal features of the second cell.

7. The method of claim 6, wherein the plurality of temporal features of the first cell and the plurality of temporal features of the second cell are selected from a group consisting of a temperature, a humidity, and a pressure.

8. A computer system tar determining a location of a pollution source, where pollution measurement data acquired from communication network includes one or more client computing devices and one or more servers, the computer system comprising:

one or more processors, one or more computer-readable memories, one or more non-transitory computer-readable tangible storage medium, and program instructions stored on at least one of the one or more non-transitory tangible storage medium for execution by at least one of the one or more processors via at least one of the one or more memories, wherein the computer system of performing a method comprises:

receiving, by the one or more client computing devices, the plurality of pollution measurement data of a geographical area, a plurality of geodetic data of the geographical area, and a plurality of meteorological data of the geographical area;

generating, by the one or more client computing devices, a grid of the geographical area, wherein the generated grid virtually divides the geographical area into a plurality of cells;

associating, by the one or more client computing devices, the plurality of the pollution measurement data, the plurality of the geodetic data, and the plurality of the meteorological data with one or more of the plurality of the cells in the generated grid;

determining, by the one or more client computing devices, a pollutant contribution value of the one or more of the plurality of the cells based on subtracting a physical contribution of the plurality of pollutants from the pollution measurement data associated with the cell, wherein the pollutant contribution is calculated including an original emission of a pollutant and a secondary formation of the pollutant inside the one or more of the plurality of the cells excluding a movement of pollutant from adjoining cells;

identifying, by the one or more client computing devices, the pollution source based on a paired comparison of the plurality of cells, wherein the paired comparison of the plurality of the cells to eliminate the pollution contributions due to the secondary formation in the cells; and displaying, by the one or more client computing devices, the location on the geographical area associated with the identified pollution source.

9. The computer system of claim 8, wherein determining the pollutant contribution value of the cell comprises:

determining the physical contribution of a plurality of pollutants of the plurality of cells based on a vertical movement and a horizontal movement of the plurality of pollutants, wherein the vertical movement is determined by a vertical wind measurement extracted from the plurality of meteorological data, and wherein the horizontal movement is determined by a horizontal wind measurement extracted from the plurality of meteorological data; and calculating the pollutant contribution value of the cell based on subtracting the physical contribution of the plurality of pollutants from the pollution measurement data associated with the cell.

10. The computer system of claim 8, wherein identifying the pollution source based on the paired comparison of the plurality of cells comprises:

determining a first cell from the plurality of cells based on a cell number;

determining a second cell from the plurality of cells based on a similarity coefficient being above a static threshold value, wherein the similarity coefficient is determined based on spatial features of the first cell and the spatial features of the second cell;

determining that a first cell pollution contribution value is higher than a second cell pollution contribution value; and based on determining the first cell pollution contribution value is higher than the second cell pollution contribution value, identifying the pollution source as the first cell.

11. The computer system of claim 10, wherein the spatial features are selected from a group consisting of a percentage representation of a plurality of mountains area within the plurality of cells, a percentage representation of a plurality of urban infrastructures area within the plurality of cells, a percentage representation of a plurality of crop fields area within the plurality of cells, a percentage representation of a forest area within the plurality of cells, a percentage representation of a plurality of grass fields area within the plurality of cells, and a percentage representation of a plurality of water reservoirs area within the plurality of cells.

12. The computer system of claim 10, wherein determining that the first cell pollution contribution value is higher than the second cell pollution contribution value comprises:

determining a dynamic similarity coefficient between the first cell and the second cell; and determining that the first cell pollution contribution value is higher than the second cell based on the dynamic similarity coefficient and the first cell pollution contribution value.

13. The computer system of claim 12, wherein the dynamic similarity coefficient is determined based on a plurality of temporal features of the first cell and a plurality of temporal features of the second cell.

14. The computer system of claim 13, wherein the plurality of temporal features of the first cell and the plurality of temporal features of the second cell are selected from a group consisting of a temperature value of a plurality of air, a humidity value of the plurality of air, and a pressure value of the plurality of air.

15. A computer program product for determining a location of a pollution source, where pollution measurement data acquired from communication network includes one or more client computing devices and one or more servers, the computer program product comprising:

one or more non-transitory computer-readable tangible storage medium and program instructions stored on at least one of the one or more non-transitory tangible storage medium, the program instructions executable by a processor, comprises:

receiving, by one or more client computing devices, a plurality of pollution measurement data of a geographical area, a plurality of geodetic data of the geographical area, and a plurality of meteorological data of the geographical area;

generating, by the one or more client computing devices, a grid of the geographical area, wherein the generated grid virtually divides the geographical area into a plurality of cells;

associating by the one or more client computing devices, the plurality of the pollution measurement data, the plurality of the geodetic data, and the plurality of the meteorological data with one or more of the plurality of the cells in the generated grid;

determining, by the one or more client computing devices, a pollutant contribution value of the one or more of the plurality of the cells based on subtracting a physical contribution of the plurality of pollutants from the pollution measurement data associated with the cell wherein the pollutant contribution is calculated including an original emission of a pollutant and a secondary formation of the pollutant inside the one or more of the plurality of the cells excluding a movement of pollutant from adjoining cells;

identifying, by the one or more client computing devices, the pollution source based on a paired comparison of the plurality of cells, wherein the paired comparison of the plurality of the cells to eliminate the pollution contributions due to secondary formation in the cell; and displaying, by the one or more client computing devices, the location on the geographical area associated with the identified pollution source.

16. The computer program product of claim 15, wherein program instructions to determine the pollutant contribution value of the cell comprises:

program instructions to determine the physical contribution of a plurality of pollutants of the plurality of cells based on a vertical movement and a horizontal movement of the plurality of pollutants, wherein the vertical movement is determined by a vertical wind measurement extracted from the plurality of meteorological data, and wherein the horizontal movement is determined by a horizontal wind measurement extracted from the plurality of meteorological data; and program instructions to calculate the pollutant contribution value of the cell based on subtracting the physical contribution of the plurality of pollutants from the pollution measurement data associated with the cell.

17. The computer program product of claim 15, wherein program instructions to identify the pollution source based on the paired comparison of the plurality of cells comprises:

program instructions to determine a first cell from the plurality of cells based on a cell number;

program instructions to determine a second cell from the plurality of cells based on a similarity coefficient being above a static threshold value, wherein the similarity coefficient is determined based on spatial features of the first cell and the spatial features of the second cell;

program instructions to determine that a first cell pollution contribution value is higher than a second cell pollution contribution value; and based on determining the first cell pollution contribution value is higher than the second cell pollution contribution value, program instructions to identify the pollution source as the first cell.

18. The computer program product of claim 17, wherein the spatial features are selected from a group consisting of a percentage representation of a plurality of mountains area within the plurality of cells, a percentage representation of a plurality of urban infrastructures area within the plurality of cells, a percentage representation of a plurality of crop fields area within the plurality of cells, a percentage representation of a forest area within the plurality of cells, a percentage representation of a plurality of grass fields area within the plurality of cells, and a percentage representation of a plurality of water reservoirs area within the plurality of cells.

19. The computer program product of claim 17, wherein program instructions to determine that the first cell pollution contribution value is higher than the second cell pollution contribution value comprises:

program instructions to determine a dynamic similarity coefficient between the first cell and the second cell; and program instructions to determine that the first cell pollution contribution value is higher than the second cell based on the dynamic similarity coefficient and the first cell pollution contribution value.

20. The computer program product of claim 19, wherein the dynamic similarity coefficient is determined based on a plurality of temporal features of the first cell and a plurality of temporal features of the second cell.

* * * * *